US012683016B2

(12) United States Patent
Takahashi

(10) Patent No.: US 12,683,016 B2
(45) Date of Patent: Jul. 14, 2026

(54) MEDICAL IMAGE PROCESSING DEVICE, MEDICAL IMAGE PROCESSING SYSTEM, MEDICAL IMAGE PROCESSING METHOD, AND PROGRAM

(71) Applicant: FUJIFILM Corporation, Tokyo (JP)

(72) Inventor: Azuma Takahashi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 170 days.

(21) Appl. No.: 18/460,579

(22) Filed: Sep. 3, 2023

(65) Prior Publication Data

US 2023/0410994 A1 Dec. 21, 2023

Related U.S. Application Data

(63) Continuation of application No. PCT/JP2022/006750, filed on Feb. 18, 2022.

(30) Foreign Application Priority Data

Mar. 24, 2021 (JP) ................................. 2021-050336

(51) Int. Cl.
*G16H 40/20* (2018.01)
*G16H 30/40* (2018.01)
(52) U.S. Cl.
CPC ............. *G16H 40/20* (2018.01); *G16H 30/40* (2018.01)
(58) Field of Classification Search
CPC ............................... G16H 40/20; G16H 30/40
See application file for complete search history.

(56) References Cited

U.S. PATENT DOCUMENTS 10,025,479 B2 7/2018 Zhao et al.
10,818,048 B2 10/2020 Zhao et al.
(Continued)

FOREIGN PATENT DOCUMENTS

JP 2004049615 2/2004
JP 2014193193 10/2014
(Continued)

OTHER PUBLICATIONS

Jorritsma et al., Adaptive support for user interface customization: a study in radiology, 77 Int J of Human-Computer Studies 1-9 (May 2015) (Year: 2015).*
Doshi et al., Abstract for: Utility of an Automated Radiology-Pathology Feedback Tool, 16(9.A) J of the American College of Radiology 1211-1217 (Sep. 2019) (Year: 2019).*
(Continued)

*Primary Examiner* — Jordan L Jackson
(74) *Attorney, Agent, or Firm* — JCIPRNET

(57) ABSTRACT

An object is to provide a medical image processing device, a medical image processing system, a medical image processing method, and a program for presenting a usage status of image processing that is settable for automatic execution. At least one processor and at least one memory storing a command to be executed by the at least one processor are provided. The at least one processor is configured to: collect usage information by a user for a result of first image processing, which is for assisting in diagnosis of a medical image and which is settable as automatic execution image processing to be automatically executed on the input medical image, and accompanying information on the medical image which is a target of the first image processing; and display the usage information and the accompanying information in association with each other on a display.

8 Claims, 5 Drawing Sheets

(56) References Cited

U.S. PATENT DOCUMENTS

| | | | |
|---|---|---|---|
| 2005/0245804 A1 | 11/2005 | Shinohara et al. | |
| 2013/0166256 A1* | 6/2013 | Wirx-Speetjens | G06F 30/00 |
| | | | 703/1 |
| 2015/0089365 A1* | 3/2015 | Zhao | G06F 3/04847 |
| | | | 715/708 |
| 2019/0286481 A1* | 9/2019 | Gatayama | G16H 40/63 |

FOREIGN PATENT DOCUMENTS

| | | |
|---|---|---|
| JP | 6230811 | 11/2017 |
| JP | 2018161488 | 10/2018 |

OTHER PUBLICATIONS

Stefanidis et al., Radiological, epidemiological and clinical patterns of pulmonary viral infections, 136 European J of Radiology (Jan. 14, 2021) (Year: 2021).*

Medverd et al., Advanced Medical Imaging Protocol Workflow—A Flexible Electronic Solution to Optimize Process Efficiency, Care Quality and Patient Safety in the National VA Enterprise 26 J Digit Imaging 643-650 (Year: 2013).*

"International Search Report (Form PCT/ISA/210) of PCT/JP2022/006750," mailed on May 10, 2022, with English translation thereof, pp. 1-5.

"Written Opinion of the International Searching Authority (Form PCT/ISA/237) of PCT/JP2022/006750," mailed on May 10, 2022, with English translation thereof, pp. 1-6.

* cited by examiner

THE NUMBER
OF TIMES OF PROCESSING

THE NUMBER OF USES

THE NUMBER
OF PREVENTED MISSES

SLICE THICKNESS [mm]

MEDICAL IMAGE PROCESSING DEVICE, MEDICAL IMAGE PROCESSING SYSTEM, MEDICAL IMAGE PROCESSING METHOD, AND PROGRAM

CROSS-REFERENCE TO RELATED APPLICATIONS

The present application is a Continuation of PCT International Application No. PCT/JP2022/006750 filed on Feb. 18, 2022 claiming priority under 35 U.S.C § 119(a) to Japanese Patent Application No. 2021-050336 filed on Mar. 24, 2021. Each of the above applications is hereby expressly incorporated by reference, in its entirety, into the present application.

BACKGROUND OF THE INVENTION

1. Field of the Invention

The present invention relates to a medical image processing device, a medical image processing system, a medical image processing method, and a program, and particularly, to a technique for presenting a usage status of automatically executed image processing.

2. Description of the Related Art

Cloud services that provide image processing services are known. For example, JP2018-161488A discloses a cloud server that provides advanced image processing services of medical images to clients, such as a medical institution doctor, an instructor, a student, an insurance company agent, a patient, or a medical researcher.

SUMMARY OF THE INVENTION

In a usage-based billing calculation processing system observed in cloud services or the like, the number of times of processing is directly linked to an amount paid by a user. In the usage-based billing calculation processing systems, it is assumed that, in a case of a system which automatically selects image processing based on image information, such as tag information and site information, and which automatically executes the selected image processing, a certain number of processing results may be subject to billing even though the results are not utilized. In addition, in a case of a flat-rate billing calculation processing system, calculation costs are incurred for a portion of the results that are not utilized. Therefore, in order to reduce expenses for the user, it is necessary to set an execution condition such that unused image processing is not executed. However, in order for the user to optimally set the execution condition, it is necessary to scrutinize an enormous data set of unused image processing and images, which poses a problem of high workload.

The present invention has been made in view of such circumstances, and an object of the present invention is to provide a medical image processing device, a medical image processing system, a medical image processing method, and a program for presenting a usage status of image processing that is settable for automatic execution.

An aspect of a medical image processing device for achieving the above object is a medical image processing device comprising: at least one processor; and at least one memory storing a command to be executed by the at least one processor, in which the at least one processor is configured to: collect usage information by a user for a result of first image processing, which is for assisting in diagnosis of a medical image and which is settable as automatic execution image processing to be automatically executed on the input medical image, and accompanying information on the medical image which is a target of the first image processing; and display the usage information and the accompanying information in association with each other on a display. According to the aspect, since the usage status of the image processing that is settable as the automatic execution image processing to be automatically executed can be presented, the user can determine whether or not to set the image processing as the automatic execution image processing based on the presented usage status.

It is preferable that the usage information includes at least one of whether or not the user has referred to the result of the first image processing, whether or not the result of the first image processing has contributed to preventing missing a disease, a reduction amount in image interpretation time due to the result of the first image processing, whether or not a measurement result of the first image processing has contributed to improvement in accuracy, or whether or not the user has issued an instruction to execute the first image processing other than the automatic execution.

It is preferable that the target of the first image processing is a tomographic image, and the accompanying information includes at least one of a slice thickness or the number of slices.

It is preferable that the at least one processor is configured to accept at least one of deletion of the first image processing from setting as the automatic execution image processing or setting of the first image processing as the automatic execution image processing.

It is preferable that the at least one processor is configured to propose an automatic execution condition for the automatic execution of the first image processing based on the usage information and the accompanying information.

It is preferable that the at least one processor is configured to propose the automatic execution condition in consideration of an external factor. In addition, it is preferable that the external factor includes seasonality of a disease targeted by the first image processing.

It is preferable that the at least one processor is configured to execute image processing set as the automatic execution image processing.

An aspect of a medical image processing system for achieving the above object is a medical image processing system comprising: the medical image processing device described above; and a server that executes image processing set as the automatic execution image processing.

An aspect of a medical image processing method for achieving the above object is a medical image processing method comprising: collecting usage information by a user for a result of first image processing, which is for assisting in diagnosis of a medical image and which is settable as automatic execution image processing to be automatically executed on the input medical image, and accompanying information on the medical image which is a target of the first image processing; and displaying the usage information and the accompanying information in association with each other on a display. According to the aspect, since the usage status of the image processing that is settable as the automatic execution image processing to be automatically executed can be presented, the user can determine whether or not to set the image processing as the automatic execution image processing based on the presented usage status.

An aspect of a program for achieving the above object is a program for causing a computer to execute the medical image processing method described above. The aspect may also include a computer-readable non-transitory storage medium on which the program is recorded. According to the aspect, since the usage status of the image processing that is settable as the automatic execution image processing to be automatically executed can be presented, the user can determine whether or not to set the image processing as the automatic execution image processing based on the presented usage status.

According to the present invention, the user can determine whether or not to set the image processing as the automatic execution image processing based on the presented usage status.

DESCRIPTION OF THE PREFERRED EMBODIMENTS

Hereinafter, preferred embodiments of the present invention will be described in detail with reference to the accompanying drawings.

[Overall Configuration of Medical Image Processing System]

Figure 1:
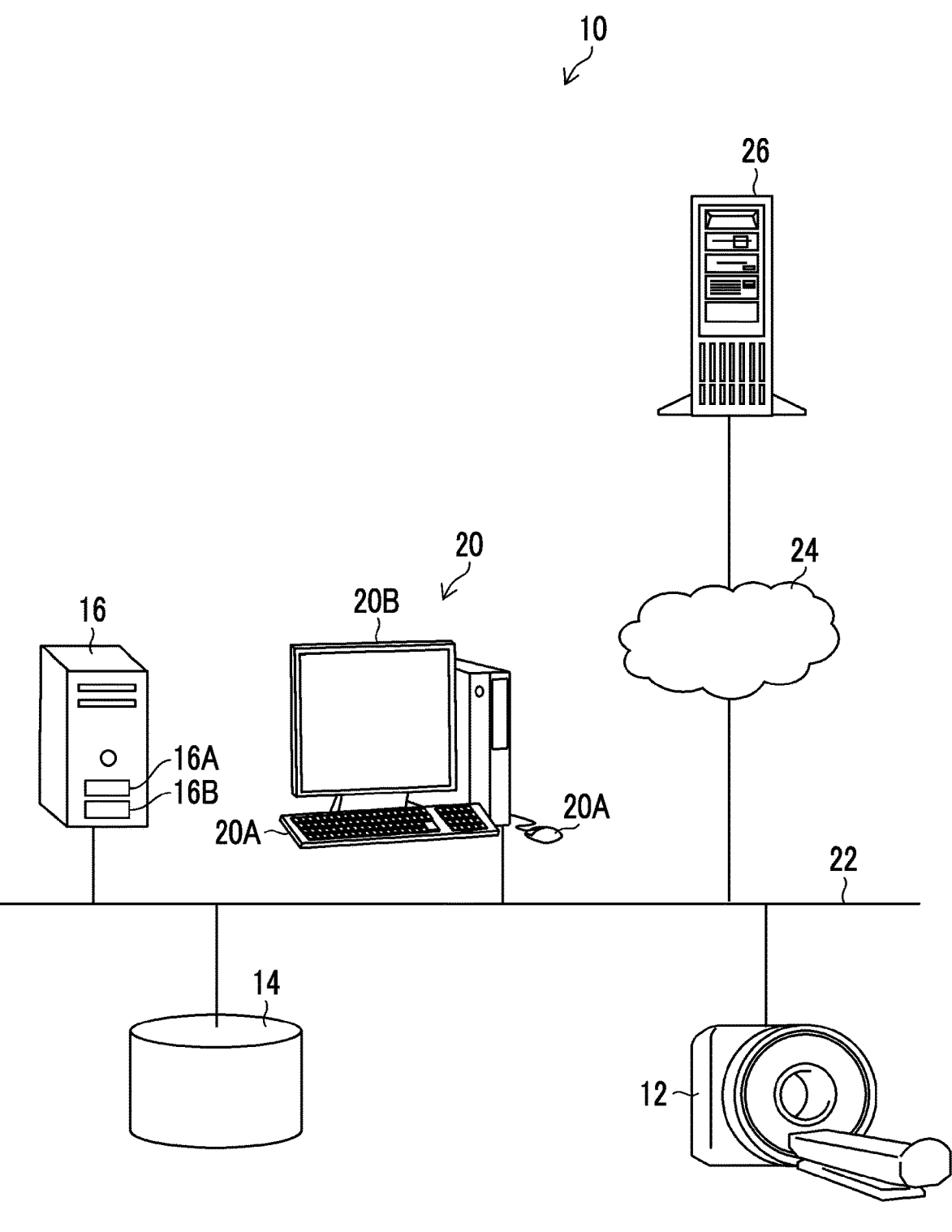
FIG. 1 is an overall configuration diagram of a medical image processing system.

FIG. 1 is an overall configuration diagram of a medical image processing system 10. The medical image processing system 10 is a system that captures an image of an examination target (patient) and that automatically executes image processing which is for assisting in diagnosis of a medical image for the captured image and which is set as automatic execution image processing. As shown in FIG. 1, the medical image processing system 10 comprises a medical image examination device 12, a medical image database 14, an image processing evaluation device 16, a user terminal 20, and a cloud server 26.

The medical image examination device 12, the medical image database 14, the image processing evaluation device 16, and the user terminal 20 are provided in a medical institution, such as a hospital, and are connected to each other via an in-hospital network 22 so as to be able to transmit and receive data. As the in-hospital network 22, a local area network (LAN) can be applied. The in-hospital network 22 may be wired or wireless.

The in-hospital network 22 is connected to the Internet 24 via a router (not shown). The in-hospital network 22 and the cloud server 26 are connected to each other via the Internet 24 so as to be able to transmit and receive data.

The medical image examination device 12 is an imaging device that images an examination target site of the examination target to generate a medical image. The medical image examination device 12 includes, for example, at least one of an X-ray imaging device, a computed tomography (CT) device, a magnetic resonance imaging (MRI) device, a positron emission tomography (PET) device, an ultrasonic device, or a computed radiography (CR) device using a planar X-ray detector.

The medical image database 14 is a database for managing medical images captured by the medical image examination device 12. As the medical image database 14, a computer comprising a high-capacity storage device can be applied. Software for providing functions of a database management system is incorporated into the computer.

As a format of the medical image, a digital imaging and communications in medicine (DICOM) standard can be applied. DICOM tag information defined by the DICOM standard may be added to the medical image. Note that the term "image" in the present specification can include the meaning of image data, which is a signal representing an image, in addition to the meaning of an image itself such as a photograph.

The image processing evaluation device 16 is an example of a medical image processing device, collects a usage status of image processing executed in the cloud server 26, and evaluates the image processing based on the usage status. As the image processing evaluation device 16, a personal computer or a workstation can be applied. The image processing evaluation device 16 comprises a processor 16A and a memory 16B. The processor 16A executes a command stored in the memory 16B.

As a hardware structure of the processor 16A, various processors described below are used. The various processors include a central processing unit (CPU) which is a general-purpose processor that executes software (programs) to act as various functional units, a graphics processing unit (GPU) which is a processor specialized in image processing, a programmable logic device (PLD) which is a processor whose circuit configuration is changeable after manufacture, such as a field-programmable gate array (FPGA), and a dedicated electric circuit which is a processor that has a dedicated circuit configuration designed to execute specific processing, such as an application-specific integrated circuit (ASIC).

One processing unit may be composed of one of the various processors or may be composed of two or more processors of the same type or different types (for example, a combination of a plurality of FPGAs, a combination of a CPU and an FPGA, or a combination of a CPU and a GPU). Alternatively, the plurality of functional units may be composed of one processor. A first example in which a plurality of functional units are composed of one processor is an aspect in which one or more CPUs and software are combined to constitute one processor and the processor acts as the plurality of functional units, as typified by a computer, such as a client and a server. A second example of the configuration is an aspect in which a processor that realizes functions of an entire system including the plurality of functional units with one integrated circuit (IC) chip is used, as typified by a system-on-chip (SoC). As described above, as the hardware structure of the various functional units, one or more of the various processors are used.

Further, as the hardware structure of the various processors, more specifically, an electric circuit (circuitry) in which circuit elements, such as semiconductor elements, are combined is used.

The memory 16B stores a command executed by the processor 16A. The memory 16B includes a random-access memory (RAM) and a read-only memory (ROM) (not shown). The processor 16A uses the RAM as a work area to execute software using various programs and parameters including a medical image processing program stored in the ROM, and executes various types of processing of the image processing evaluation device 16 using the parameters stored in the ROM.

The user terminal 20 is a terminal device used by a user, such as a doctor, and, for example, a known image viewer for image interpretation is applied. The user terminal 20 may be a personal computer, a workstation, or a tablet terminal. The user terminal 20 comprises an input device 20A and a display 20B. The medical image captured by the medical image examination device 12 and a result of the image processing are displayed on the display 20B. In addition, information related to the image processing, which is presented by the image processing evaluation device 16, is displayed on the display 20B. The user can input an instruction to the medical image processing system 10 using the input device 20A.

As the cloud server 26, for example, a server computer, a personal computer, or a workstation can be applied. The cloud server 26 performs image processing including at least one of lesion extraction or disease name determination processing on the medical image as the examination target. The cloud server 26 can be accessed from the in-hospital networks 22 of a plurality of hospitals via the Internet 24. In the present embodiment, processing performed in the cloud server 26 is a usage-based billing cloud service. The processing performed in the cloud server 26 may be a flat-rate billing cloud service.

[Functional Configuration of Medical Image Processing System]

Figure 2:
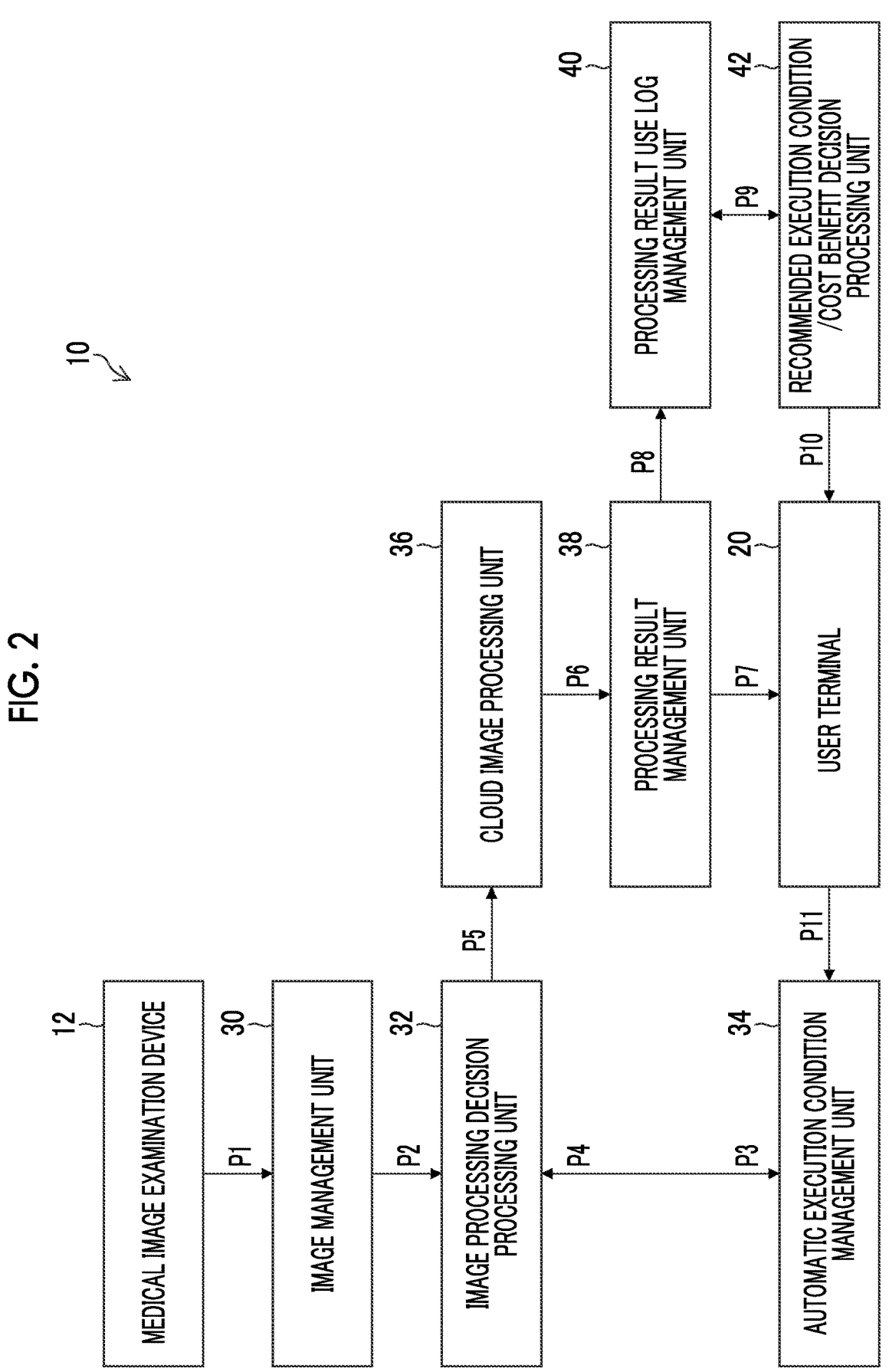
FIG. 2 is a diagram showing a functional configuration and a processing process of the medical image processing system.

FIG. 2 is a diagram showing a functional configuration and a processing process of the medical image processing system 10. The processing process will be described later. As shown in FIG. 2, the medical image processing system 10 comprises an image management unit 30, an image processing decision processing unit 32, an automatic execution condition management unit 34, a cloud image processing unit 36, a processing result management unit 38, a processing result use log management unit 40, and a recommended execution condition/cost benefit decision processing unit 42, in addition to the medical image examination device 12 and the user terminal 20 shown in FIG. 1.

A function of the image management unit 30 is realized by the medical image database 14. Functions of the image processing decision processing unit 32, of the automatic execution condition management unit 34, of the processing result management unit 38, of the processing result use log management unit 40, and of the recommended execution condition/cost benefit decision processing unit 42 are realized by the image processing evaluation device 16. A function of the cloud image processing unit 36 is realized by the cloud server 26.

The image management unit 30 manages medical images captured by the medical image examination device 12. The image processing decision processing unit 32 decides on automatic execution image processing to be automatically executed on the medical image captured by the medical image examination device 12. The automatic execution condition management unit 34 holds an automatic execution condition of the automatic execution image processing. The cloud image processing unit 36 executes image processing on the medical image captured by the medical image examination device 12.

The image processing executed by the cloud image processing unit 36 is not limited as long as it is image processing on a medical image. For example, computer-aided diagnosis (CAD) for extracting a lesion or the like in the medical image; segmentation processing of a site, a lesion, or the like; labeling processing of a site name, a disease name, or the like; similar image search; and similar case search are included.

The processing result management unit 38 acquires an execution result of the image processing executed by the cloud image processing unit 36. The processing result use log management unit 40 stores, as a log, usage information by the user for the result of the image processing and accompanying information on the medical image which is a target of the image processing. That is, the processing result use log management unit 40 stores, as a log, the usage information indicating the usage status by the user for the result of the image processing, and the accompanying information on the medical image which is the target of the image processing. The recommended execution condition/cost benefit decision processing unit 42 decides on a recommended execution condition of the image processing and its cost benefit based on the logs accumulated in the processing result use log management unit 40.

[Medical Image Processing Method]

Figure 3:
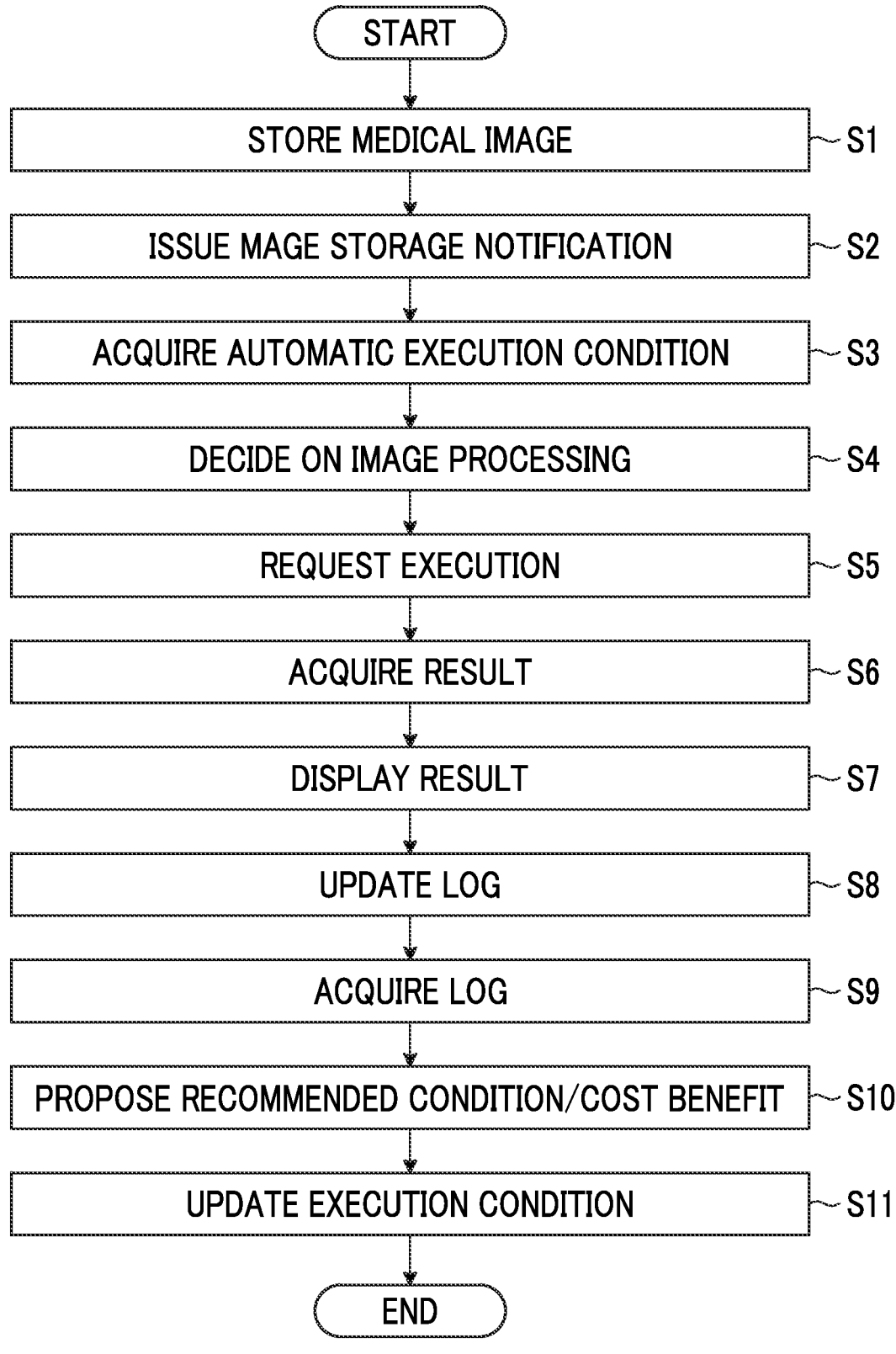
FIG. 3 is a flowchart showing a medical image processing method using the medical image processing system.

FIG. 3 is a flowchart showing a medical image processing method using the medical image processing system 10. The medical image processing method is realized by the processor 16A executing the medical image processing program stored in the memory 16B. The medical image processing program may be provided by a computer-readable non-transitory storage medium. In this case, the image processing evaluation device 16 may read the medical image processing program from the non-transitory storage medium and store the medical image processing program in the memory 16B. Hereinafter, the processing process of the medical image processing system 10 and the medical image processing method will be described with reference to FIGS. 2 and 3.

In step S1, the medical image examination device 12 captures the medical image of the patient and stores the captured medical image in the image management unit 30 (process P1). For example, a doctor uses a CT device (not shown) as the medical image examination device 12 to capture a CT image (an example of a "tomographic image") of the patient. Here, it is assumed that the CT device captures a CT image with a slice thickness of 1 mm and with the number of slices of 1000. The CT device stores the captured CT image in the image management unit 30.

In step S2, the image management unit 30 notifies the image processing decision processing unit 32 that the medical image has been stored by the medical image examination device 12 (process P2). Here, the image management unit 30 notifies the image processing decision processing unit 32 that the CT image has been imported from the CT device.

In step S3, the image processing decision processing unit 32 acquires, from the automatic execution condition management unit 34, the automatic execution condition of the automatic execution image processing to be automatically executed (process P3).

For example, it is assumed that, among a plurality of types of image processing (an example of "first image processing") that are settable as the automatic execution image processing by the cloud image processing unit 36, types of image processing set as the automatic execution image processing are "CAD (1)", "CAD (2)", "segmentation (1)", "labeling (1)", and "labeling (2)". The image processing decision processing unit 32 acquires each automatic execution condition of five types of image processing. The cloud image processing unit 36 executes the automatic execution image processing on an image satisfying the automatic execution condition. The automatic execution condition includes, for example, at least one of the slice thickness or the number of slices of the CT image. Here, an example will be described in which the automatic execution condition is set using the slice thickness and the number of slices.

Parameters of the automatic execution conditions are not limited to the slice thickness and the number of slices of the tomographic image. For example, as the parameters of the automatic execution condition, field of view (FOV), spacing, processing for a past image, image type (primary image or secondary image), description, device information (manufacturer), patient information (sex and age), contrast information, radiant exposure information, reconstruction information, or the like may be used.

In step S4, the image processing decision processing unit 32 decides on image processing to be executed on the CT image stored in step S1 in accordance with the automatic execution condition acquired in step S3 (process P4).

Here, the CT image stored in step S1 has a slice thickness of 1 mm and the number of slices of 1000, as described above. For example, in a case where the automatic execution condition of "CAD (1)" is that the slice thickness is 0.5 mm or greater and the number of slices is 100 or more, the CT image stored in step S1 satisfies the automatic execution condition of "CAD (1)". Therefore, the image processing decision processing unit 32 selects "CAD (1)" as the image processing to be executed. In addition, in a case where the automatic execution condition of "CAD (2)" is that the slice thickness is 5 mm or greater and the number of slices is 1000 or more, the CT image stored in step S1 does not satisfy the automatic execution condition of "CAD (2)". Therefore, the image processing decision processing unit 32 does not select "CAD (2)" as the image processing to be executed.

In step S5, the image processing decision processing unit 32 requests the execution of the image processing decided on in step S4 to the cloud image processing unit 36 (process P5).

In step S6, the cloud image processing unit 36 acquires the CT image stored in the image management unit 30 in step S1 and executes the image processing requested in step S5 on the CT image. Further, the processing result management unit 38 acquires the execution result of the image processing from the cloud image processing unit 36 (process P6).

In step S7, the user terminal 20 acquires the execution result of the image processing from the processing result management unit 38 and displays the execution result on the display 20B in accordance with an operation from the user (process P7).

In step S8, the processing result use log management unit 40 stores, as the log, the usage information, which is information indicating that the user has used the execution result in step S7, and the accompanying information on the CT image on which the image processing has been executed (process P8). The usage information includes at least one of whether or not the user has referred to the result of the image processing, whether or not the result of the image processing has contributed to preventing missing a disease, a reduction amount in image interpretation time due to the result of the image processing, whether or not a measurement result of the image processing has contributed to improvement in accuracy, or whether or not the user has issued an instruction to execute the image processing other than the automatic execution. The accompanying information includes at least one of the slice thickness or the number of slices of the CT image.

Here, the processing result use log management unit 40 stores the log of the automatically executed image processing and also stores the log of the image processing executed in response to a manual instruction from the user other than the automatic execution.

As the medical image processing system 10 repeats the processing of steps S1 to S8, the processing result use log management unit 40 accumulates logs. In step S9 (an example of a "collection step"), the recommended execution condition/cost benefit decision processing unit 42 acquires the accumulated logs (process P9).

In step S10, the recommended execution condition/cost benefit decision processing unit 42 calculates an evaluation value of the image processing based on the accumulated logs and decides on a recommended condition of the automatic execution condition and its effect. Instead of using all the accumulated logs, the evaluation value may be calculated using the latest log for a certain period (for example, for one week). The accumulation period of the log to be used for the calculation may be settable for each hospital.

Further, the recommended execution condition/cost benefit decision processing unit 42 displays and proposes the decided-on recommended condition and its effect on the display 20B (process P10).

For example, in a case where the evaluation value of "CAD (1)" is low, the recommended condition is displayed as "'CAD (1)' is considered to be unnecessary". In a case where the evaluation value when the slice thickness of "CAD (1)" is 1 to 3 mm is low, it may be displayed as "'CAD (1)' is unnecessary" for the CT image with a slice thickness of 1 to 3 mm.

In step S11, the user confirms the recommended condition and its effect displayed on the display 20B of the user terminal 20 and sets the automatic execution condition using the input device 20A. The user may set the displayed recommended condition as the automatic execution condition as it is or may set a desired automatic execution condition with reference to the displayed recommended condition. Finally, the user terminal 20 stores the set automatic execution condition in the automatic execution condition management unit 34 (process P11). Thereafter, the image processing decision processing unit 32 acquires a newly set automatic execution condition.

[Proposal Screen of Recommended Condition/Cost Benefit]

Figures 4, 5:
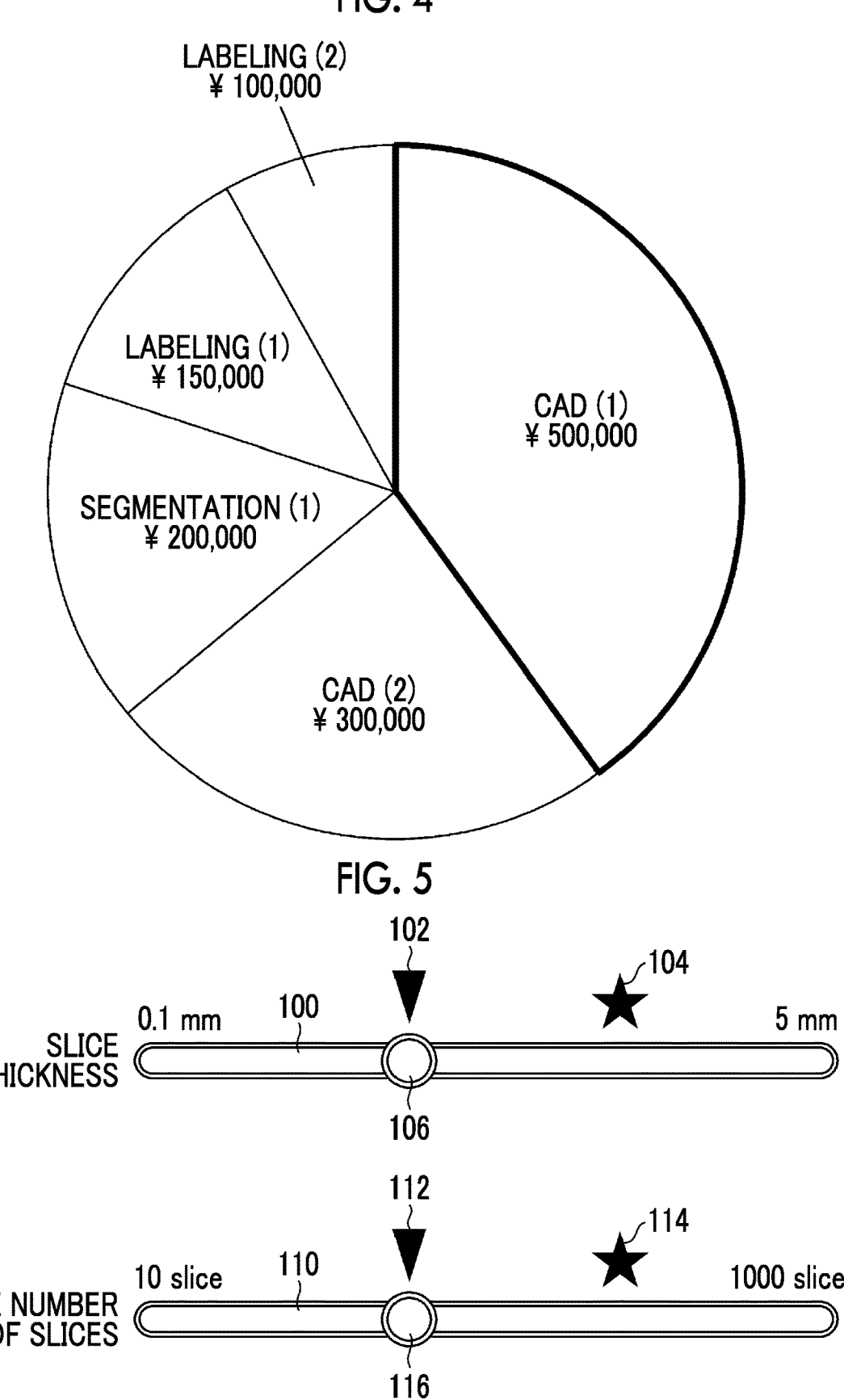
FIG. 4 is an example of a proposal screen of recommended conditions and cost benefits.
FIG. 5 is an example of a display screen of an automatic execution condition of "CAD (1)".

FIG. 4 is an example of a proposal screen of a recommended condition/cost benefit displayed on the display 20B of the user terminal 20. Here, a pie graph shows a proportion of the latest cost for a certain period for each of "CAD (1)", "CAD (2)", "segmentation (1)", "labeling (1)", and "labeling (2)", which are types of image processing automatically executed by the cloud image processing unit 36, and each cost amount is displayed in the pie graph.

Each region of the pie graph can be selected by the input device 20A. Here, a thick frame surrounding "CAD (1)" indicates that it is currently selected.

FIG. 5 is an example of a display screen of the automatic execution condition of "CAD (1)" displayed in a case where "CAD (1)" is selected in the pie graph of FIG. 4 displayed on the display 20B. In the present embodiment, the automatic execution condition is the slice thickness and the number of slices, and the display of the automatic execution condition includes a scroll bar 100 representing the automatic execution condition of the slice thickness and a scroll bar 110 representing the automatic execution condition of the number of slices. The pie graph of FIG. 4 and a slider bar of FIG. 5 may be simultaneously displayed on the same screen.

The scroll bar 100 indicates a range of the slice thickness from 0.1 mm to 5 mm. A triangular mark 102 displayed above the scroll bar 100 indicates a lower limit value of the currently set automatic execution condition. Therefore, an image on a right side of a position of the mark 102 (with a greater slice thickness than the value indicated by the mark 102) is an image as the target of the automatic execution. In addition, a star-shaped mark 104 indicates a lower limit value of the automatic execution condition to be recommended by the recommended execution condition/cost benefit decision processing unit 42, and an image on the right side of a position of the mark 104 is an image as the target of the execution condition to be recommended.

For example, the currently set automatic execution condition of the slice thickness is 0.5 mm or greater, and the recommended automatic execution condition is 2 mm or greater. An upper limit value of the slice thickness may be set as the automatic execution condition.

In addition, the scroll bar 100 includes a knob 106 that is movable in the range of the scroll bar 100. The user can change the automatic execution condition by dragging the knob 106 using the input device 20A to change a position of the knob 106. Here, an image on the right side of the position of the knob 106 is an image as the target of the automatic execution image processing.

For example, in a case where the knob 106 is moved from a position of 0.5 mm to a position of 2 mm, the automatic execution condition of the slice thickness is changed from 0.5 mm or greater to 2 mm or greater. After this change of the automatic execution condition, the image processing is not automatically executed for the tomographic image having a slice thickness of 0.5 mm to 2 mm, and it is expected that the cost in the cloud service based on usage is reduced accordingly by that amount. The recommended execution condition/cost benefit decision processing unit 42 recalculates the latest cost for a certain period of "CAD (1)" in a case where the automatic execution condition of the slice thickness of "CAD (1)" is changed from 0.5 mm or greater to 2 mm or greater, and reflects the recalculated cost in the pie graph shown in FIG. 4.

Meanwhile, the scroll bar 110 indicates a range of the number of slices from 10 to 1000. A triangular mark 112 displayed above the scroll bar 110 indicates a lower limit value of the currently set automatic execution condition. Therefore, an image on the right side of a position of the mark 112 (with a greater number of slices than the value indicated by the mark 112) is an image as the target of the automatic execution. In addition, a star-shaped mark 114 indicates a lower limit value of the automatic execution condition to be recommended by the recommended execution condition/cost benefit decision processing unit 42, and an image on the right side of a position of the mark 114 is an image as the target of the execution condition to be recommended.

For example, the currently set automatic execution condition of the number of slices is 100 or more, and the recommended automatic execution condition is 200 or more. As the automatic execution condition, an upper limit value of the number of slices may be set.

In addition, the scroll bar 110 includes a knob 116 that is movable in the range of the scroll bar 110. The user can change the automatic execution condition by dragging the knob 116 using the input device 20A to change a position of the knob 116. Here, an image on the right side of the position of the knob 116 is an image as the target of the automatic execution image processing.

For example, in a case where the knob 116 is moved from the position of 100 slices to the position of 200 slices, the automatic execution condition of the number of slices is changed from 100 or more to 200 or more. The recommended execution condition/cost benefit decision processing unit 42 recalculates the latest cost for a certain period of "CAD (1)" in a case where the automatic execution condition of the number of slices of "CAD (1)" is changed from 100 or more to 200 or more, and reflects the recalculated cost in the pie graph shown in FIG. 4.

As described above, the user can confirm the cost benefit in a case where the automatic execution condition is changed.

Here, the change of the automatic execution condition of "CAD (1)" has been described, but the automatic execution condition is settable for each image processing. In the present embodiment, in addition to "CAD (1)", each of the automatic execution conditions of "CAD (2)", "segmentation (1)", "labeling (1)", and "labeling (2)" can be set.

On the screen shown in FIG. 4, the automatic execution condition management unit 34 may accept deletion of image processing to be automatically executed, from the input device 20A. Further, the automatic execution condition management unit 34 may accept addition of image processing to be automatically executed, from the input device 20A. For example, the user can use the input device 20A to add processing of similar image search and of similar case search to the image processing to be automatically executed.

[Calculation of Evaluation Value]

The recommended execution condition/cost benefit decision processing unit 42 may propose the automatic execution condition in consideration of an external factor. The external factor includes seasonality of a disease targeted by image processing. The recommended execution condition/cost benefit decision processing unit 42 calculates an evaluation value in consideration of the external factor of image processing by using, for example, the following equations.

$$\text{Evaluation Value } a1 = (\text{Number of Uses})/(\text{Number of Times of Processing})$$

$$\text{Evaluation Value } a2 = (\text{Number of Prevented Misses})/(\text{Number of Times of Processing})$$

$$\text{Evaluation Value } a3 = (\text{Seasonality Evaluation of Image Processing}) \times (\text{Seasonal Coefficient})$$

$$\text{Final Evaluation Value } a4 = a1 + a2 + a3$$

Here, the number of times of processing is the number of times of case imaging in which image processing is performed by the cloud image processing unit 36, the number of uses is the number of times the user has confirmed the execution result on the user terminal 20 (the number of times of display on the display 20B), and the number of prevented misses is the number of lesions that have been missed by the user but have been found by image processing. In the number of prevented misses, for example, the user performs diagnosis without using the execution result of the image processing, the execution result is displayed on the display 20B after the diagnosis, and the number of lesions not included in the diagnosis of the user among the displayed lesions is counted.

The seasonality evaluation of the image processing is a value indicating the presence or absence of seasonality of occurrence of the disease targeted by the image processing. The seasonal coefficient is a coefficient having a relatively larger value for a season in which the number of occurrences of the disease targeted by the image processing is relatively larger. For example, in a case of a disease that occurs relatively frequently in winter, the seasonal coefficient of the image processing of the disease has a relatively larger value in winter.

It is proposed to maintain the image processing as the automatic execution image processing in a case where the final evaluation value a4 is equal to or greater than a predetermined threshold value, and to delete the image processing from the automatic execution image processing in a case where the final evaluation value a4 is less than the threshold value. In a case where any one of the evaluation value a1, a2, or a3 is equal to or greater than the threshold value, the image processing may be maintained as the automatic execution image processing.

As the evaluation value, a calculation function of a quality-adjusted life year (QALY) may be used.

[Evaluation Item Other than Time Shortening/Prevented Misses]

The recommended execution condition/cost benefit decision processing unit 42 may propose setting as the automatic execution condition or deletion in consideration of other evaluation items, such as improvement of measurement accuracy as the usage information.

For example, it is assumed that "a doctor has determined a volume of a lesion was $X_1$ [cm$^3$] without confirming the result of the image processing, and a result of volume measurement of the image processing executed by the cloud image processing unit 36 was $X_2$ [cm$^3$] different from $X_1$ [cm$^3$]".

In this case, in a case where the processing result use log management unit 40 stores, as the usage information, a log indicating that "the doctor has corrected an image interpretation report after confirming the result of the volume measurement of the image processing executed by the cloud image processing unit 36", the recommended execution condition/cost benefit decision processing unit 42 determines that "the volume measurement of the image processing is superior to that of the doctor and has contributed to the improvement of the measurement accuracy", and recommends setting the image processing in which the volume measurement has been performed, as the automatic execution image processing.

On the other hand, in a case where the processing result use log management unit 40 stores, as the usage information, a log indicating that "the doctor has not corrected the image interpretation report even after confirming the result of the volume measurement of the image processing executed by the cloud image processing unit 36", the recommended execution condition/cost benefit decision processing unit 42 determines that "the volume measurement of the doctor is superior to that of the image processing and the image processing has not contributed to the improvement of the accuracy", and recommends deleting the image processing in which the volume measurement has been performed, from setting as the automatic execution image processing.

As described above, it is possible to improve the measurement accuracy of the image interpretation by recommending the image processing that has contributed to the improvement of the measurement accuracy, such as the volume measurement, as the automatic execution image processing. The present invention is not limited to the improvement of the measurement accuracy, and the recommended execution condition/cost benefit decision processing unit 42 can propose setting as the automatic execution condition or deletion according to a contribution degree of each evaluation item regarding the image interpretation of the medical image.

[Associated Display of Usage Information and Accompanying Information]

The medical image processing system 10 may display the collected usage information and accompanying information in association with each other on the display 20B (an example of a "presentation step").

Figure 6:
FIG. 6 is an example of an aggregation results screen for logs.

FIG. 6 is an example of an aggregation results screen for logs, which has been accumulated by the processing result use log management unit 40, displayed on the display 20B. In this example, for the log of "CAD (1)", the usage information for each accompanying information is shown in a frequency line graph, and specifically, the number of times of processing [unit: slices], the number of uses [unit: slices], and the number of prevented misses [unit: locations] for each slice thickness are shown.

In a case where the slice thickness is 0.1 to 1 mm (equal to or greater than 0.1 mm and less than 1 mm), the number of times of processing is 1000 slices, but the number of uses is 0 slices. Therefore, the number of prevented misses is 0 locations (because the population is 0). In a case where the slice thickness is 1 to 3 mm (equal to or greater than 1 mm and less than 3 mm), the number of times of processing is 2000 slices, the number of uses is 1600 slices, and the number of prevented misses is 2000 locations. In a case where the slice thickness is 3 to 5 mm (equal to or greater than 3 mm and less than 5 mm), the number of times of processing is 1000 slices, the number of uses is 0 slices, and the number of prevented misses is 0 locations. In a case where the slice thickness is 5 mm or greater (equal to or greater than 5 mm), the number of times of processing is 2000 slices, the number of uses is 1800 slices, and the number of prevented misses is 1000 locations.

From this graph, it is considered that a case where the slice thickness is 0.1 to 1 mm and a case where the slice thickness is 3 to 5 mm do not need to be automatically executed and are not appropriate as the automatic execution condition because the result of the image processing is not used. On the other hand, it can be seen that a case where the slice thickness is 1 to 3 mm and a case where the slice thickness is equal to or greater than 5 mm are useful for the prevented misses and are appropriate as the automatic execution condition.

Here, the number of times of processing, the number of uses, and the number of prevented misses for each slice thickness have been shown, but the same log aggregation results may be also displayed for the number of slices.

In the medical image processing system 10, the user can confirm the condition suitable for the automatic execution condition of the automatic execution image processing by displaying the log aggregation results on the display 20B. In addition, the log aggregation results can also be used for the introduction cost of the cloud service and for the selection of the plan that should be first contracted for the cloud service.

In the case of this example, the recommended execution condition/cost benefit decision processing unit 42 may not only display the log aggregation results, but also present a case where the slice thickness is 1 to 3 mm and a case where the slice thickness is equal to or greater than 5 mm as the recommended condition of the automatic execution condition.

The following (1) to (11) are described in the above embodiment.

(1) An aspect of a medical image processing device is a medical image processing device comprising: at least one processor; and at least one memory storing a command to be executed by the at least one processor, in which the at least one processor is configured to: collect usage information by a user for a result of first image processing, which is for assisting in diagnosis of a medical image and which is settable as automatic execution image processing to be automatically executed on the input medical image, and accompanying information on the medical image which is a target of the first image processing; and display the usage information and the accompanying information in association with each other on a display. That is, an aspect of the medical image processing device is a medical image processing device comprising: at least one processor; and at least one memory storing a command to be executed by the at least one processor, in which the at least one processor is configured to: collect usage information indicating a usage status by a user for a result of first image processing, which is for assisting in diagnosis of a medical image and which is settable as automatic execution image processing to be automatically executed on the input medical image, and accompanying information on the medical image which is a target of the first image processing; and display the usage information and the accompanying information in association with each other on a display. According to the aspect, since the usage status of the image processing that is settable as the automatic execution image processing to be automatically executed can be presented, the user can determine whether or not to set the image processing as the automatic execution image processing based on the presented usage status.

(2) It is preferable that the usage information includes at least one of whether or not the user has referred to the result of the first image processing, whether or not the result of the first image processing has contributed to preventing missing a disease, a reduction amount in image interpretation time due to the result of the first image processing, whether or not a measurement result of the first image processing has contributed to improvement in accuracy, or whether or not the user has issued an instruction to execute the first image processing other than the automatic execution. As a result, it is possible to collect the usage information reflecting the contribution degree of the image processing.

(3) It is preferable that the target of the first image processing is a tomographic image, and the accompanying information includes at least one of a slice thickness or the number of slices. As a result, it is possible to collect at least one of the slice thickness or the number of slices of the tomographic image.

(4) It is preferable that the at least one processor is configured to accept at least one of deletion of the first image processing from setting as the automatic execution image processing or setting of the first image processing as the automatic execution image processing. As a result, it is possible to, as the automatic execution image processing, delete unnecessary first image processing and set necessary first image processing.

(5) It is preferable that the at least one processor is configured to propose an automatic execution condition for the automatic execution of the first image processing based on the usage information and the accompanying information. As a result, the user can know an appropriate automatic execution condition.

(6) It is preferable that the at least one processor is configured to propose the automatic execution condition in consideration of an external factor. As a result, it is possible to propose an appropriate automatic execution condition.

(7) In addition, it is preferable that the external factor includes seasonality of a disease targeted by the first image processing. As a result, it is possible to propose an appropriate automatic execution condition.

(8) It is preferable that the at least one processor is configured to execute image processing set as the automatic execution image processing. As a result, it is possible to automatically execute the set image processing.

(9) An aspect of a medical image processing system is a medical image processing system comprising: the medical image processing device according to (1) to (8); and a server that executes image processing set as the automatic execution image processing. According to the aspect, since the usage status of the image processing that is settable as the automatic execution image processing to be automatically executed can be presented, the user can determine whether or not to set the image processing as the automatic execution image processing based on the presented usage status, and can automatically execute the image processing set as the automatic execution image processing.

(10) An aspect of a medical image processing method is a medical image processing method comprising: collecting usage information by a user for a result of first image processing, which is for assisting in diagnosis of a medical image and which is settable as automatic execution image processing to be automatically executed on the input medical image, and accompanying information on the medical image which is a target of the first image processing; and displaying the usage information and the accompanying information in association with each other on a display. That is, an aspect of the medical image processing method is a medical image processing method comprising: collecting usage information indicating a usage status by a user for a result of first image processing, which is for assisting in diagnosis of a medical image and which is settable as automatic execution image processing to be automatically executed on the input medical image, and accompanying information on the medical image which is a target of the first image processing; and displaying the usage information and the accompanying information in association with each other on a display. According to the aspect, since the usage status of the image processing that is settable as the automatic execution image processing to be automatically executed can be presented, the user can determine whether or not to set the image processing as the automatic execution image processing based on the presented usage status.

(11) An aspect of a program for achieving the above object is a program for causing a computer to execute the medical image processing method described above. The aspect may also include a computer-readable non-transitory storage medium on which the program is recorded. According to the aspect, since the usage status of the image processing that is settable as the automatic execution image processing to be automatically executed can be presented, the user can determine whether or not to set the image processing as the automatic execution image processing based on the presented usage status.

OTHER

The technical scope of the present invention is not limited to the scope described in the above embodiments. The configurations and the like in each embodiment can be appropriately combined between the respective embodiments without departing from the gist of the present invention.

EXPLANATION OF REFERENCES

10: medical image processing system
12: medical image examination device

15

14: medical image database
16: image processing evaluation device
16A: processor
16B: memory
20: user terminal
20A: input device
20B: display
22: in-hospital network
24: Internet
26: cloud server
30 image management unit
32: image processing decision processing unit
34: automatic execution condition management unit
36: cloud image processing unit
38: processing result management unit
40: processing result use log management unit
42: recommended execution condition/cost benefit deci-
    sion processing unit
100: scroll bar
102: mark
104: mark
106: knob
110: scroll bar
112: mark
114: mark
116: knob
P1 to P11: process of medical image processing device
S1 to S11: step of medical image processing method

What is claimed is:

1. A medical imaging processing system comprising:
a 3D imaging device, configured to capture a tomographic
    image; and
a medical image processing device comprising:
at least one processor; and
at least one memory storing a command to be executed by
    the at least one processor and an access log that records
    usage information of a user for results of image pro-
    cessing,
wherein the at least one processor is configured to:
    receive the tomographic image from the 3D imaging
        device;
    perform automatic execution image processing on the
        tomographic image satisfying an automatic execu-
        tion condition,
        wherein the automatic execution condition is at least
            one of slice thickness of the tomographic image
            being greater than a first threshold or a number of
            slices of the tomographic images being greater
            than a second threshold,
        wherein the automatic execution image processing
            comprises a plurality of types of image processing
            for assisting in diagnosis of the tomographic and
            which are settable as automatic execution image
            processing to be automatically executed on the
            tomographic image, and
        wherein the plurality of types of image processing
            comprise lesion extraction, segmentation process-
            ing, and labelling processing;
    retrieve the usage information of the user from the
        access log stored in the at least one memory to
        determine whether or not the user has referred to a
        result of first image processing, among the plurality
        of types of image processing, and accompanying
        information on the tomographic image which is a
        target of the first image processing;

display the usage information and the accompanying
    information in association with each other on a
    display; and
in response to the result of first image processing not
    being referred by the user, execute the automatic
    execution image processing without executing the
    first image processing.
2. The medical image processing system according to
claim 1,
wherein the usage information includes at least one of
    whether or not the user has referred to the result of the
    first image processing, whether or not the result of the
    first image processing has contributed to preventing
    missing a disease, a reduction amount in image inter-
    pretation time due to the result of the first image
    processing, whether or not a measurement result of the
    first image processing has contributed to improvement
    in accuracy, or whether or not the user has issued an
    instruction to execute the first image processing other
    than the automatic execution.
3. The medical image processing system according to
claim 1,
wherein the at least one processor is configured to
perform the automatic execution condition further in
    consideration of an external factor.
4. The medical image processing system according to
claim 3,
wherein the external factor includes seasonality of a
    disease targeted by the first image processing.
5. The medical image processing system according to
claim 1 further comprising:
a server that executes the automatic execution image
    processing.
6. The medical image processing system according to
claim 1,
wherein the 3D imaging device is at least one of an X-ray
    imaging device, a computed tomography (CT) device,
    a magnetic resonance imaging (MRI) device, a positron
    emission tomography (PET) device, an ultrasonic
    device, or a computed radiography (CR) device.
7. A medical image processing method comprising:
storing an access log that records usage information of a
    user for results of image processing in at least one
    memory;
receiving a tomographic image from a 3D imaging device
    that captures the tomographic image;
performing automatic execution image processing on the
    tomographic image satisfying an automatic execution
    condition,
    wherein the automatic execution condition is at least
        one of slice thickness of the tomographic image
        being greater than a first threshold or a number of
        slices of the tomographic images being greater than
        a second threshold,
    wherein the automatic execution image processing
        comprises a plurality of types of image processing
        for assisting in diagnosis of the tomographic and
        which are settable as automatic execution image
        processing to be automatically executed on the tomo-
        graphic image, and
    wherein the plurality of types of image processing
        comprise lesion extraction, segmentation processing,
        and labelling processing;
retrieving the usage information of the user from the
    access log stored in the at least one memory to deter-
    mine whether or not the user has referred to a result of
    first image processing, among the plurality of types of image processing, and accompanying information on the tomographic image which is a target of the first image processing;

displaying the usage information and the accompanying information in association with each other on a display; and in response to the result of first image processing not being referred by the user, executing the automatic execution image processing without executing the first image processing.

8. A non-transitory, computer-readable tangible recording medium which records thereon a program for causing, when read by a computer, the computer to execute the medical image processing method according to claim 7.

* * * * *